United States Patent
Ting (10) Patent No.: US 10,653,305 B2
(45) Date of Patent: May 19, 2020

(54) IMAGE PROCESSING SYSTEM AND ENDOSCOPE USING THE SAME

(71) Applicant: OPCOM INC., New Taipei (TW)

(72) Inventor: Chih-Yu Ting, New Taipei (TW)

(73) Assignee: OPCOM INC., New Taipei (TW)

( * ) Notice: Subject to any disclaimer, the term of this patent is extended or adjusted under 35 U.S.C. 154(b) by 7 days.

(21) Appl. No.: 16/136,162

(22) Filed: Sep. 19, 2018

(65) Prior Publication Data

US 2019/0159664 A1    May 30, 2019

Related U.S. Application Data

(60) Provisional application No. 62/590,447, filed on Nov. 24, 2017.

(51) Int. Cl.

| | |
|---|---|
| H04N 9/47 | (2006.01) |
| A61B 1/04 | (2006.01) |
| A61B 1/05 | (2006.01) |
| A61B 1/00 | (2006.01) |
| A61B 1/045 | (2006.01) |
| H04N 13/00 | (2018.01) |
| A61B 1/005 | (2006.01) |
| H04N 5/225 | (2006.01) |

(52) U.S. Cl.
CPC ............ *A61B 1/05* (2013.01); *A61B 1/00009* (2013.01); *A61B 1/00174* (2013.01); *A61B 1/045* (2013.01); *A61B 1/00006* (2013.01); *A61B 1/00039* (2013.01); *A61B 1/0051* (2013.01); *A61B 1/00096* (2013.01); *G06T 2207/10068* (2013.01); *H04N 2005/2255* (2013.01)

(58) Field of Classification Search
USPC .................................. 348/65, 72, 61, 45, 42
See application file for complete search history.

(56) References Cited

U.S. PATENT DOCUMENTS

| 9,526,080 B2 * | 12/2016 | Khait | ..................... A61B 5/061 |
| 2007/0252893 A1 * | 11/2007 | Shigemori | ......... A61B 1/00009 348/65 |

* cited by examiner

*Primary Examiner* — Daquan Zhao
(74) *Attorney, Agent, or Firm* — Winston Hsu (57) ABSTRACT

An image processing system includes an image sensor receiving light beams to output an output signal corresponding to a horizontal scan period and an image processor electronically connecting to the image sensor and including a signal interceptor and a calculating unit. The image processor transforms the output signal to generate a combining signal. The signal interceptor intercepts a first part of the combining signal corresponding to a first clock period of the horizontal scan period to obtain a first signal and intercepts a second part of the combining signal corresponding to a second clock period of the horizontal scan period to obtain a second signal. The calculating unit calculates the first signal and the second signal to obtain an image pixel data according to a differential calculation. The number of clocks of the first clock period is the same as the number of clocks of the second clock period.

20 Claims, 4 Drawing Sheets

IMAGE PROCESSING SYSTEM AND ENDOSCOPE USING THE SAME

CROSS REFERENCE TO RELATED APPLICATIONS

This application claims the benefit of U.S. Provisional Application No. 62/590,447, which was filed on Nov. 24, 2017, and is incorporated herein by reference.

BACKGROUND OF THE INVENTION

1. Field of the Invention

The invention relates in general to an image processing system, and more particularly to the image processing system of an endoscope which has a smaller size of an image sensor.

2. Description of the Prior Art

Currently, an endoscope usually includes a distal end, an insert tube, a handle and a cable, wherein, the insert tube, the handle and the cable are connected to each other. The distal end is disposed in one end of the insert tube, and two ends of the handle connect between the other end of the insert tube and the cable. The endoscope may have a camera module which includes a camera, and the camera may be disposed in the distal end for observing, capturing images of the affected part of the patient or displaying to the main system.

The camera module is necessary for the endoscope; therefore, it has become an imminent task to provide high image resolution of the camera module. If the image resolution of the camera module needs to be increased, the size of the image sensor of the camera needs to be increasing for obtaining high image resolution. When the size of the camera is increasing, the size of the distal end may be increasing for receiving the camera, and the whole endoscope may be increasing.

However, when the size of the distal end is increasing, the size of the connection relationship between the distal end and the insert tube may be increasing and the cost may be increasing. When the patient is in the endoscopic surgery, the size of the wound of the patient for inserting the endoscope may be greater than or equal to an inside diameter of the distal end. Therefore, when the inside diameter of the distal end is greater in accordance with the necessary, the size of the wound of the patient may not be reduce and burden on a patient may not be reduced.

If the size of the distal end is reduced for reducing the burden on the patient, the size of the camera has to be reduced, and meanwhile, the image resolution is reduced. The user may not have a good observation caused by the images captured from the camera with the low resolution and may reduce the exact determination of the operation of the surgery or cause of disease.

SUMMARY OF THE INVENTION

The disclosure is directed to an image processing system and the endoscope using the same. The image processing system has the image sensor and the image processor, and the image sensor may be disposed in the distal end and the image processor may be disposed in the handle or the main device.

According to one aspect of the present disclosure, an image processing system is provided. The image processing system includes an image sensor and an image processor. The image sensor receives a plurality of light beams to output an output signal corresponding to a horizontal scan period. The image processor electronically connects to the image sensor and includes a signal interceptor and a calculating unit. The image processor transforms the output signal to generate a combining signal. The signal interceptor intercepts a first part of the combining signal corresponding to a first clock period of the horizontal scan period to obtain a first signal and intercepts a second part of the combining signal corresponding to a second clock period of the horizontal scan period to obtain a second signal. The calculating unit calculates the first signal and the second signal to obtain an image pixel data in accordance with a differential calculation, wherein, the number of clocks of the first clock period is the same as the number of clocks of the second clock period.

According to another aspect of the present disclosure, an endoscope is provided. The endoscope includes an insert tube, a handle, an image processing system and a distal end. One end of the handle connects to one end of the insert tube. The image processing system includes an image sensor and an image processor. The image sensor receives a plurality of light beams to output an output signal corresponding to a horizontal scan period. The image processor electronically connects to the image sensor and includes a signal interceptor and a calculating unit, and the image processor transforms the output signal to generate a combining signal. The signal interceptor intercepts a first part of the combining signal corresponding to a first clock period of the horizontal scan period to obtain a first signal, and intercepts a second part of the combining signal corresponding to a second clock period of the horizontal scan period to obtain a second signal. The calculating unit calculates the first signal and the second signal to obtain an image pixel data in accordance with a differential calculation. The number of clocks of the first clock period is the same as the number of clocks of the second clock period, and the image processor is disposed in the handle. One end of the distal end connects to the other end of the insert tube. The image sensor is disposed in the distal end.

According to another aspect of the present disclosure, an endoscope is provided. The endoscope electronically connects to a main device and includes an insert tube, a handle, an image processing system and a distal end. One end of the handle connects to one end of the insert tube. The image processing system includes an image sensor and an image processor. The image sensor receives a plurality of light beams to output an output signal corresponding to a horizontal scan period. The image processor electronically connects to the image sensor and includes a signal interceptor and a calculating unit. The image processor transforms the output signal to generate a combining signal. The signal interceptor intercepts a first part of the combining signal corresponding to a first clock period of the horizontal scan period to obtain a first signal and intercepts a second part of the combining signal corresponding to a second clock period of the horizontal scan period to obtain a second signal, and the calculating unit calculates the first signal and the second signal to obtain an image pixel data in accordance with a differential calculation. The number of clocks of the first clock period is the same as the number of clocks of the second clock period, and the image processor is disposed in the main device. One end of the distal end connects to the other end of the insert tube. The image sensor is disposed in the distal end.

By the features described above, the present invention provides an image processing system and the endoscope using the same, the image sensor transforms the light beams to the output signal or reducing the size of the image sensor, and the protocol of the output signal may be defined as necessary, and the image processor may preform from the processing of the output signal to the image frame, and the image sensor may be disposed in the distal end of the endoscope, and the image processor and the other elements of the endoscope may be disposed in the handle or the main device connecting to the endoscope; the size of the whole endoscope may be reduced in accordance with the smaller size of the image sensor, and the smaller size of the image sensor images performed completely; the image sensor has the smaller size for saving the cost and increases the image resolution to maintain the quality of the images.

These and other objectives of the present invention will no doubt become obvious to those of ordinary skill in the art after reading the following detailed description of the preferred embodiment that is illustrated in the various figures and drawings.

DETAILED DESCRIPTION

Preferred embodiments are disclosed below for elaborating the invention. Various lengths, such as optical focus lengths or distances, of a plurality of micro lenses are applied on a plurality of detecting pixels, such that in an autofocus process, the time consumption can be reduced, and the accuracy can be improved. The following embodiments are for the purpose of elaboration only, not for limiting the scope of protection of the invention. Besides, secondary elements are omitted in the following embodiments to highlight the technical features of the invention.

Figure 1:
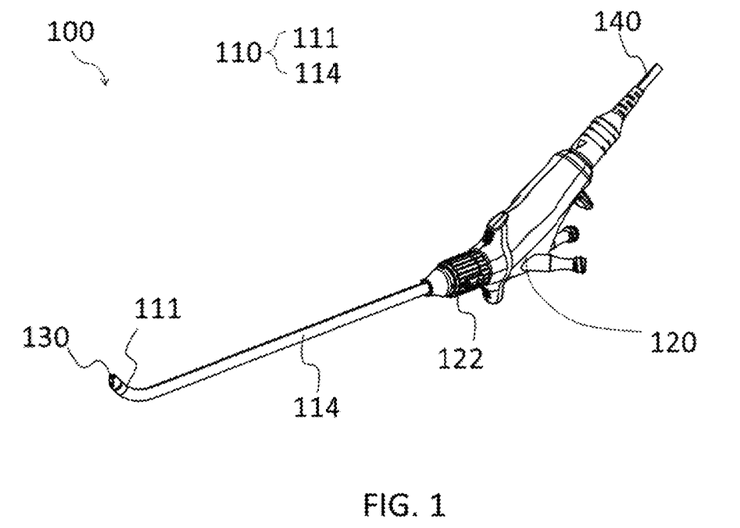
FIG. 1 is a side view schematically showing a whole endoscope according to one embodiment of the present invention.
Figure 2:
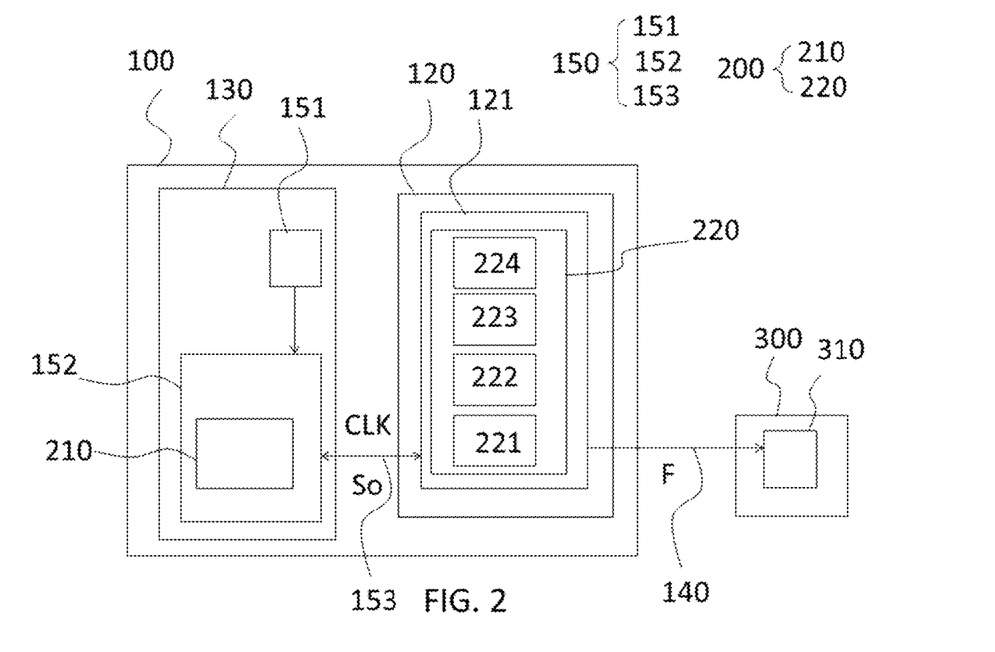
FIG. 2 is a block diagram schematically showing the endoscope of FIG. 1.

Reference is now made to FIG. 1, which is a side view schematically showing a whole endoscope according to one embodiment of the present invention; FIG. 2, which is a block diagram schematically showing the endoscope of FIG. 1. As shown in FIG. 1 and FIG. 2, an endoscope 100 includes an image processing system 200, an insert tube 110, a handle 120, a distal end 130 and a cable 140. Wherein, one end of the handle 120 connects to one end of the insert tube 110, and the other end of the handle 120 connects to one end of the cable 140, and one end of the distal end 130 connects to the other end of the insert tube 110. The endoscope 100 may be a disposable endoscope or a reusable endoscope. The disposable endoscope or the reusable endoscope may be chosen in accordance with user's needed. The insert tube 110 may be a flexible tube or an inflexible tube. But the present invention is not limited to the embodiments explained above.

In the current embodiment, the insert tube 110 may include a bending section 111 and an extending section (no shown), and the insert section 111 and the extending section construct a catheter. The insert tube 110 further includes a first cladding unit (no shown) and a second cladding unit 114. The first cladding unit into which the catheter is inserted, the second cladding unit 114 into which the first cladding unit is inserted. In other words, the first cladding unit may be configured to cover the outer face of the catheter, and the second cladding unit 114 may be configured to cover the outer face of the first cladding unit tightly. In one embodiment, the first cladding unit substantially may be a braid which is a net-like tube, disposed so as to cover an outer of catheter. The second cladding unit 114 is made of, for example, a plastic material or a silicone material. The second cladding unit 114 may be a heat shrink tubing. When the second cladding unit 114 covers the outer of the first cladding unit, the second cladding unit 114 may be fixed on the first cladding unit formed by a heating process or a processing which is provided to shrink the whole second cladding unit 114 for protecting the insert tube 110. In the other embodiment, the catheter of the insert tube 110 may provide at least one instrument channel. But the present invention is not limited to the embodiments explained above.

The handle 120 further includes a first circuit board 121, a rotating unit (no shown), a controlling unit (no shown) and an operating unit 122. The handle 120 further includes a space (no shown) formed therein. The first circuit board 121 and the rotating unit are received in the space of the handle 120. The operating unit 122 is disposed on the outer of the handle 120 and connects to the rotating unit. The rotating unit and the bending section 111 of the insert tube 110 are connected with each other in accordance with the controlling unit disposed through the catheter of the insert tube 110. When the operating unit 122 may be controlled to move in accordance with a user, the rotating unit may be rotated in accordance with the operating unit 122 to move the controlling unit to control the bending section 111 of the insert tube 110 to bend at any angle.

The endoscope 100 further includes a camera module 150. The camera module 150 includes a camera 151, a second circuit board 152 and a wire 153. Wherein, the camera module 150 is disposed in the distal end 130. In other words, the camera 151 of the camera module 150 and the second circuit board 152 are electronically connected with each other and disposed in the distal end 130. The wire 153 electronically connects to the second circuit board 152 and the first circuit board 121 of the handle 120. The distal end 130 further connects to the catheter, and at least one instrument may further be exposed from the distal end 130 to operate different endoscopic surgeries or tests in accordance with the instrument and the camera 151.

The endoscope 100 further electronically connects to a main device 300. One end of the cable 140 connects to the first circuit board 121 of the handle 120, and the other end of the cable 140 connects to the main device 300. The camera 151 of the distal end 130 captures at least image to transfer through the wire 153 from the second circuit board 152 to the first circuit board 121 of the handle 120 to be displayed at least one monitor 310 of the main device 300 through the cable 140. In another embodiment, the endoscope 100 further includes the main device 300. But the present invention is not limited to the embodiments explained above.

In the current embodiment, the image processing system 200 is disposed in the endoscope 100 and includes an image sensor 210 and an image processor 220. In another current embodiment, the image processing system 200 may further be disposed in and applied to the endoscope 100 as necessary. But the present invention is not limited to the embodiments explained above.

In the current embodiment, the image sensor 210 receives a plurality of light beams to output an output signal So corresponding to a horizontal scan period H. In other words, the image sensor 210 receives a plurality of the clocks CLK. In the embodiment, the horizontal scan period H is formed by the clocks CLK. Therefore, the image sensor 210 receives the light beams to output the output signal So corresponding to the horizontal scan period H in accordance with the clocks CLK. Furthermore, the image sensor 210 receives the output signal So generated from the light beams during the horizontal scan period H.

In the current embodiment, the image sensor 210 further includes at least two ports (no shown). Here, the image sensor 210 is exemplified to include four ports. The ports of the image sensor 210 may be a receiving power port, a ground port, a receiving clock port and an output port, and the image sensor 210 receives the clocks CLK by the receiving clock port and output the output signal So by the output port. The size of the image sensor 210 may be reduced in the manufacturing process because of the number of the ports of the image sensor 210 is decreasing. The image sensor 210 receives the light beams to output the output signal So through the four ports in accordance with a protocol as necessary to determine the contents and the data of the output signal So, the output signal So may have a custom format. Therefore, the size of the image sensor 210 may be reduced by the custom protocol, the custom format of the output signal So and/or the ports.

The image processing system 200 includes the horizontal scan period H, a vertical scan period Vsy and a vertical scan line Vw. The horizontal scan period H includes 680 the clocks CLK, the vertical scan line Vw includes 680 the clocks CLK. In other words, the 680 the clocks CLK is determined the horizontal scan period H. The 680 the clocks CLK is determined the vertical scan line Vw. The vertical scan period Vsy is 244 the horizontal scan period H.

In another current embodiment, the clocks CLK received from the image sensor 210 may be inputted from an external inputting device or generated from the image processor 220. Here, the image processor 220 is exemplified to generate the clocks CLK to transfer to the image sensor 210.

Figure 3:
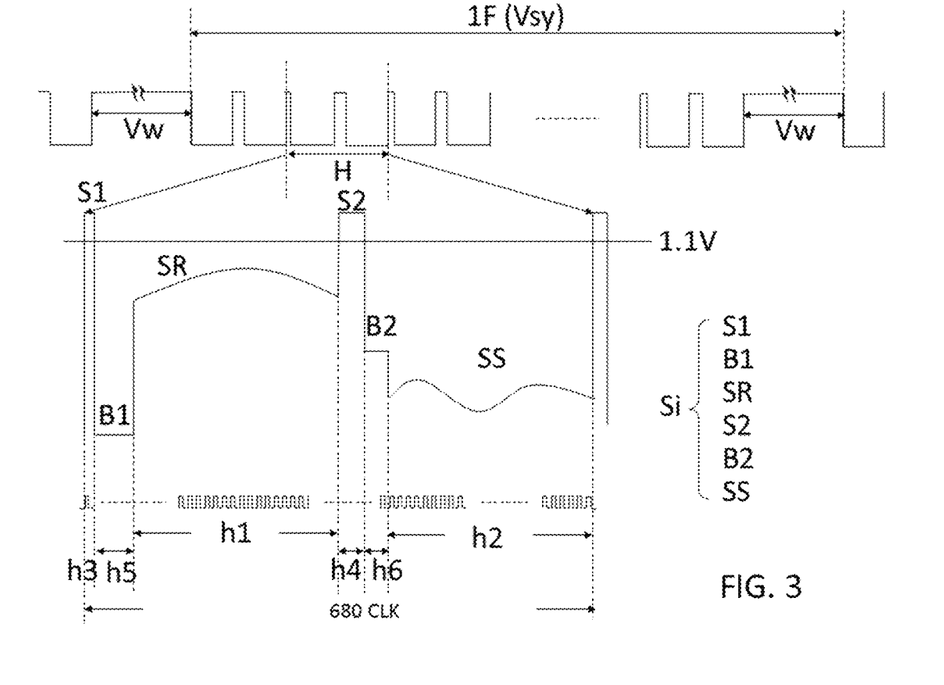
FIG. 3 is a waveform view showing the clock periods corresponds to the parts of the combining signal during the horizontal scan period, respectively, according to one embodiment of the present invention.

In the current embodiment, the horizontal scan period H further includes a first clock period h1, a second clock period h2, a third clock period h3, a fourth clock period h4, a fifth clock period h5 and a sixth clock period h6. The third clock period h3 and the fourth clock period h4 include a plurality of the clocks CLK, respectively. The fifth clock period h5 and the sixth clock period h6 include a plurality of the clocks CLK, respectively. In other words, the sum of the number of the clocks CLK of the first clock period h1, the second clock period h2, the third clock period h3, the fourth clock period h4, the fifth clock period h5 and the sixth clock period h6 is the number of the clocks CLK of the horizontal scan period H which is 680 the clocks CLK. The number of the clocks CLK of the first clock period h1 is the same as the number of the clocks CLK of the second clock period h2. The first clock period h1, the second clock period h2, the third clock period h3, the fourth clock period h4, the fifth clock period h5 and the sixth clock period h6 are not overlapped with each other.

In the current embodiment, the first clock period h1 and the second clock period h2 include 324 the clocks CLK, respectively. The third clock period h3 includes 4 the clocks CLK. The fourth clock period h4 includes 8 the clocks CLK. The fifth clock period h5 includes 12 the clocks CLK. The sixth clock period h6 includes 8 the clocks CLK. Therefore, the sum of the number of the clocks CLK of the first clock period h1, the second clock period h2, the third clock period h3, the fourth clock period h4, the fifth clock period h5 and the sixth clock period h6 is the number of the clocks CLK of the horizontal scan period H.

In another current embodiment, the first clock period h1 is the period of the 17th clock to the 340th clock of the horizontal scan period H. The second clock period h2 is the period of the 357th clock to the 680th clock of the horizontal scan period H. The third clock period h3 is the period of the first clock to the fourth clock of the horizontal scan period H. The fourth clock period h4 is the period of the 341th clock to the 348th clock of the horizontal scan period H. The fifth clock period h5 is the period of the fifth clock to the 16th clock of the horizontal scan period H. The sixth clock period h6 is the period of the 349th clock to the 356th clock of the horizontal scan period H. Therefore, each clock period h1, h2, h3, h4, h5, h6 is corresponding to a plurality of parts of the horizontal scan period H, for example, the third clock period h3, the fifth clock period h5, the first clock period h1, the fourth clock period h4, the sixth clock period h6 and the second clock period h2 are arranged in order to correspond to the horizontal scan period H. But the present invention is not limited to the embodiments explained above.

The image processor 220 electronically connects to the image sensor 210 and includes an analog-to-digital converter 221, a signal interceptor 222 and a calculating unit 223. The image processor 220 receives the output signal So and transforms the output signal So to obtain a combining signal Si. The image processor 220 further transforms the output signal So to generate the combining signal Si in accordance with the analog-to-digital converter 221. In other words, the output signal So may have an analog data, the combining signal Si may have a digital data. But the present invention is not limited to the embodiments explained above.

Reference is now made to FIG. 3, which is a waveform view showing the clock periods corresponds to the parts of the combining signal during the horizontal scan period, respectively, according to one embodiment of the present invention. As shown in FIG. 3, the combining signal Si is formed from a plurality of data. The combining signal Si may be separated a first part, a second part, a third part, a fourth part, a fifth part and a sixth part. Furthermore, the first part, the second part, the third part, the fourth part, the fifth part and the sixth part may construct the combining signal Si. The first part, the second part, the third part, the fourth part, the fifth part and the sixth part include a plurality of data, respectively. Wherein, the data may be pixels or voltage values, but the present invention is not limited to the embodiments explained above. The combining signal Si may correspond to the horizontal scan period H because of the output signal So outputted in accordance with the horizontal scan period H. Furthermore, the first part, the second part, the third part, the fourth part, the fifth part and the sixth part of the combining signal Si are corresponding to the first clock period h1, the second clock period h2, the third clock period h3, the fourth clock period h4, the fifth clock period h5 and the sixth clock period h6 of the horizontal scan period H, respectively.

In the current embodiment, the signal interceptor 222 of the image processor 220 intercepts a first part of the combining signal Si corresponding to the first clock period h1 of the horizontal scan period H which is the period of the 17th clock to the 340th clock of the horizontal scan period H to obtain a first signal SR. The signal interceptor 222 intercepts a second part of the combining signal Si corresponding to the second clock period h2 of the horizontal scan period H which is the period of the 357th clock to the 680th clock of the horizontal scan period H to obtain a second signal SS.

In the current embodiment, the signal interceptor 222 of the image processor 220 intercepts a third part of the combining signal Si corresponding to the third clock period h3 of the horizontal scan period H which is the period of the first clock to the fourth clock of the horizontal scan period H to obtain a first sync signal S1 corresponding to the first signal SR. The signal interceptor 222 intercepts a fourth part of the combining signal S1 corresponding to the fourth clock period h4 of the horizontal scan period H which is the period of the 341th clock to the 348th clock of the horizontal scan period H to obtain a second sync signal S2 corresponding to the second signal SS. The first sync signal and the second sync signal have a plurality of the clocks CLK, respectively. The first sync signal S1, the second sync signal S2, the first signal SR and the second signal SS are not overlapped with each other.

The image processor 220 further includes a comparator 224, the comparator 224 further receives the first sync signal S1 and the second sync signal S2 and determines whether the first sync signal S1 and the second sync signal S2 are greater than a threshold or not; when the first sync signal S1 and the second sync signal S2 are greater than the threshold, the comparator 224 outputs a counting signal (no shown). The values of the first sync signal S1 and the second sync signal S2 are voltage values, respectively, but the present invention is not limited to the embodiments explained above.

For example, if the first sync signal S1 and the second sync signal S2 are 1.2 voltage, and the threshold is 1.1 voltage; the signal interceptor 222 intercepts the first sync signal S1 and the second sync signal S2, and the comparator 224 determines whether the first sync signal S1 and the second sync signal S2 are greater than the threshold or not. Meanwhile, the first sync signal S1 and the second sync signal S2 which are 1.2 voltage are greater than the threshold which is 1.1 voltage. Therefore, the comparator 224 outputs the counting signal. The image processor 220 stars to count every 680 the clocks CLK to define the horizontal scan period H in accordance with the counting signal, and the image processor 220 obtains the initial first clock CLK and intercepts the first signal SR and the second signal SS in accordance with the first sync signal S1, the second sync signal S2, but the present invention is not limited to the embodiments explained above.

The signal interceptor 222 of the image processor 220 intercepts a fifth part of the combining signal Si corresponding to the fifth clock period h5 of the horizontal scan period H which is the period of the fifth clock to the 16th clock of the horizontal scan period H and intercepts a sixth part of the combining signal Si corresponding to the sixth clock period h6 of the horizontal scan period H which is the period of the 349th clock to the 356th clock of the horizontal scan period H to obtain a first blank signal B1 and a second blank signal B2. Wherein, the first blank signal B1, the second blank signal B2, the first sync signal S1, the second sync signal S2, the first signal SR and the second signal SS are not overlapped with each other. Therefore, the signal interceptor 222 of the image processor 220 intercepts the parts of the combining signal Si corresponding to the clock periods h1, h2, h3, h4, h5, h6 of the horizontal scan period H to obtain the first blank signal B1, the second blank signal B2, the first sync signal S1, the second sync signal S2, the first signal SR and the second signal SS, respectively. In other words, the first blank signal B1, the second blank signal B2, the first sync signal S1, the second sync signal S2, the first signal SR and the second signal SS are to combine to form the combining signal Si. In the embodiment, the first blank signal B1 and the second blank signal B2 are corresponding to the first signal SR and the second signal SS, respectively. The first blank signal B1 and the second blank signal B2 are arranged above the first signal SR and the second signal SS, respectively. The data of the first blank signal B1 and the second blank signal B2 may be the blank data for transferring the first signal SR and the second signal SS which coordinate the clocks CLK synchronously and stably.

In the current embodiment, the calculating unit 223 of the image processor 220 calculates the first signal SR and the second signal SS to obtain an image pixel data in accordance with a differential calculation. The image pixel data may be 324 pixels. Furthermore, the image pixel data may be obtained from the calculation of the signal interceptor 222 and the calculating unit 223 during the horizontal scan period H. Therefore, the pixels of a horizontal scan line (no shown) is the image pixel data, such as 324 pixels, but the present invention is not limited to the embodiments explained above.

For example, the image sensor 210 of the image processing system 200 receives the light beams to output the output signal So corresponding to the horizontal scan period H. The analog-to-digital converter 221 transforms the output signal So to generate the combining signal Si. The signal interceptor 222 intercepts a first part of the combining signal Si corresponding to the first clock period h1 of the horizontal scan period H to obtain the first signal SR and intercepts a second part of the combining signal Si corresponding to the second clock period h2 of the horizontal scan period H to obtain the second signal SS. The calculating unit 223 calculates the first signal SR and the second signal SS to obtain the image pixel data which is the pixels of the horizontal scan line in accordance with a differential calculation. The calculating unit 223 of the image processor 220 calculates the vertical scan period Vsy and every 244 the horizontal scan periods H to obtain an image frame F. The image processor 220 may obtain the pixels of each horizontal scan line is 324 pixels, and obtain the pixels of 244 the horizontal scan lines. Therefore, the image sensor 210 and the image processor 220 of the image processing system 200 calculate to obtain the vertical scan period Vsy during the horizontal scan period H, and the pixels of the image frame F may be about 79056 pixels which is a quotient of 324 pixels of each horizontal scan line times 244 the horizontal scan lines.

The image sensor 210 is disposed in the distal end 130 and electronically connects to the camera module 150, furthermore, the image sensor 210 is disposed in the second circuit board 152 and electronically connects to the camera 151 of the camera module 150. The image processor 220 is disposed in the handle 120 and electronically connects to the first circuit board 121. Therefore, the image processing system 200 of the endoscope 100 transforms the light beams to the image frame F and transfer to the main device 300 to display in accordance with the cable 140.

Figure 4:
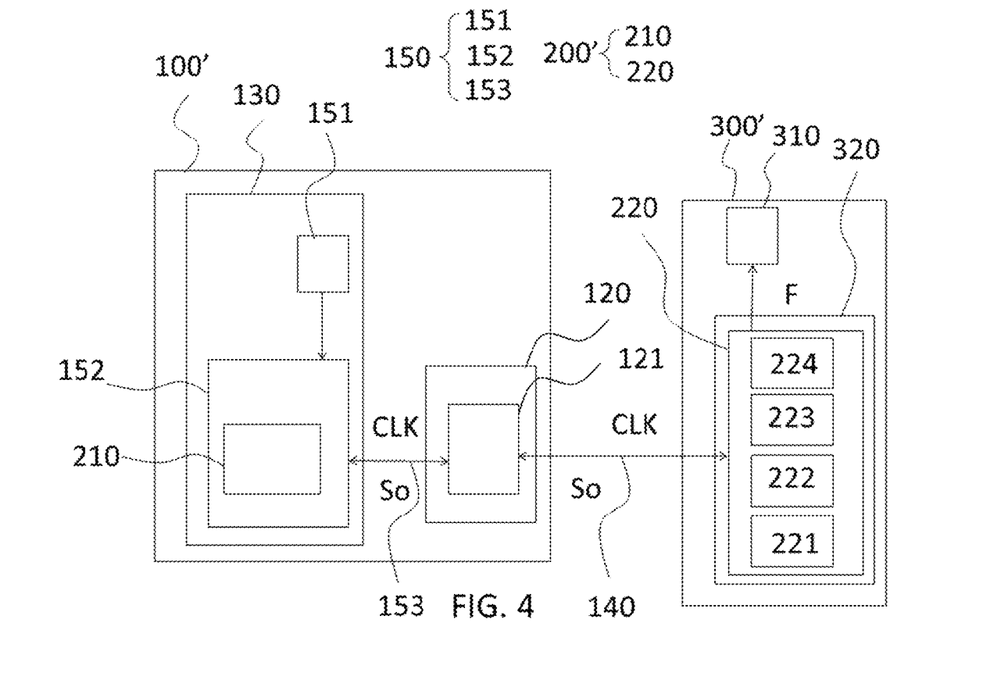
FIG. 4 is a block diagram schematically showing the endoscope according to another embodiment of the present invention.

Reference is now made to FIG. 4, which is a block diagram schematically showing the endoscope according to another embodiment of the present invention. As shown in FIG. 4, the image processing system 200' may further be applied to an endoscope 100'. The image sensor 210 of the image processing 200' is disposed in the distal end 130 and electronically connects to the camera module 150, furthermore, the image sensor 210 of the image processing 200' electronically connects to the camera 151 of the camera module 150 and is disposed in the second circuit board 152. The image processing 200' of the present invention of FIG. 4 is similar to the image processing system 200 of FIG. 2, and the same element designations and symbols are used in the present embodiment. The main difference between the image processing system 200' of FIG. 4 and the image processing system 200 of FIG. 2 is that the image processor 220 of the image processing system 200' is disposed in the main device 300', furthermore, the image processor 220 of the image processing system 200' is further disposed in a circuit board 320 of the main device 300'. Therefore, the image processing system 200' transforms the light beams to the output signal So to transfer the output signal So to the main device 300' in accordance with the cable 140. And the image processing system 200' calculates the output signal So to generate the image frame F to display on the monitor 310 of the main device 300'. As shown in FIG. 4, in another current embodiment, the image sensor 210 receives the clocks CLK which are generated from the image processor 220. Furthermore, the image processor 220 generates the clocks CLK which is transferred through the circuit board 320 of the main device 300' to the first circuit board 121 and then the clocks CLK is transferred to the second circuit board to the image sensor 210.

In another current embodiment, the image sensor 210 transforms the light beams to obtain the output signal So.

The image sensor 210 transforms the light beams to obtain the output signal So corresponding to the horizontal scan period H, and the image processor 220 disposed in the second circuit board 152 of the handle 120 of the endoscope 100 or disposed in the main device 300' of the endoscope 100' transforms the output signal So to the combining signal Si and the signal interceptor 222 of the image processor 220 intercepts the third part of the combining signal Si corresponding to the third clock period h3 of the horizontal scan period H and intercepts the fourth part of the combining signal S1 corresponding to the fourth clock period h4 of the horizontal scan period H to obtain the first sync signal S1 corresponding to the first signal SR and the second sync signal S2 corresponding to the second signal SS, respectively. Meanwhile, the comparator 224 determines that the first sync signal S1 and the second sync signal S2 are greater than the threshold and then transfer the counting signal to the calculating unit 223, and the calculating unit 223 counts every 680 the clocks CLK to be defined the horizontal scan period H in accordance with the counting signal. And then the signal interceptor 222 of the image processor 220 intercepts the first part of the combining signal Si corresponding to the first clock period h1 of the horizontal scan period H and the second part of the combining signal Si corresponding to a second clock period h2 of the horizontal scan period H to obtain the first signal SR and the second signal SS. The calculating unit 223 calculates the first signal SR and the second signal SS to obtain the image pixel data in accordance with a differential calculation. Furthermore, the image sensor 210 and the image processor 220 of the image processing system 200 calculate the vertical scan period Vsy to obtain 244 the image pixel data and output the pixels of the image frame F which is the quotient of the pixels of each horizontal scan line times the horizontal scan lines.

To summarize, the image sensor 210 transforms the light beams to the output signal So for reducing the size of the image sensor 210, and the protocol of the output signal So may be defined as necessary, and the image processor 220 may preform from the processing of the output signal So to the image frame F, and the image sensor 210 may be disposed in the distal end of the endoscope 100, 100', and the image processor 220 and the other elements of the endoscope 100, 100' may be disposed in the handle 120 or the main device 300' connecting the endoscope 100'; the size of the whole endoscope 100, 100' may be reduced in accordance with the smaller size of the image sensor 210, and the smaller size of the image sensor 210 may not influence the images performed completely; the image sensor 210 has the smaller size for saving the cost and increases the image resolution to maintain the quality of the images.

Those skilled in the art will readily observe that numerous modifications and alterations of the device and method may be made while retaining the teachings of the invention. Accordingly, the above disclosure should be construed as limited only by the metes and bounds of the appended claims.

What is claimed is:

1. An image processing system, comprising:
an image sensor receiving a plurality of light beams to output an output signal corresponding to a horizontal scan period; and
an image processor electronically connecting to the image sensor, the image processor comprising a signal interceptor and a calculating unit for processing the output signal so as to reduce a size of the image sensor, the image processor transforming the output signal to generate a combining signal, the signal interceptor intercepting a first part of the combining signal corresponding to a first clock period of the horizontal scan period to obtain a first signal and intercepting a second part of the combining signal corresponding to a second clock period of the horizontal scan period to obtain a second signal, the calculating unit calculating the first signal and the second signal to obtain an image pixel data in accordance with a differential calculation;
wherein the number of the clocks of the first clock period is the same as the number of the clocks of the second clock period.

2. The image processing system of claim 1, wherein the image pixel data is 324 pixels.

3. The image processing system of claim 1, wherein the first clock period is the period of the 17th clock to the 340th clock of the horizontal scan period, and the second clock period is the period of the 357th clock to the 680th clock of the horizontal scan period.

4. The image processing system of claim 1, wherein the image processor further comprises an analog-to-digital converter, and the image processor transforms the output signal to generate the combining signal in accordance with the analog-to-digital converter.

5. The image processing system of claim 1, wherein the horizontal scan period comprises 680 clocks.

6. The image processing system of claim 1, wherein the first clock period and the second clock period comprise 324 clocks, respectively.

7. The image processing system of claim 1, wherein the combining signal comprises a third part and a fourth part, the signal interceptor intercepts the third part and the fourth part of the combining signal corresponding to a third clock period and a fourth clock period of the horizontal scan period to obtain a first sync signal corresponding to the first signal and a second sync signal corresponding to the second signal, respectively, the first sync signal and the second sync signal have a plurality of the clocks, respectively, and the first sync signal, the second sync signal, the first signal and the second signal are not overlapped with each other.

8. The image processing system of claim 7, wherein the combining signal comprises a fifth part and a sixth part, the signal interceptor intercepts the fifth part and the sixth part of the combining signal corresponding to a fifth clock period and a sixth clock period of the horizontal scan period to obtain a first blank signal and a second blank signal, respectively, the first blank signal and the second blank signal comprise a plurality of the clocks, respectively, and the first blank signal, the second blank signal, the first sync signal, the second sync signal, the first signal and the second signal are not overlapped with each other.

9. An endoscope, comprising:
an insert tube;
a handle, one end of the handle connecting to one end of the insert tube;
an image processing system comprising an image sensor and an image processor, the image sensor receiving a plurality of light beams to output an output signal corresponding to a horizontal scan period, the image processor electronically connecting to the image sensor and comprising a signal interceptor and a calculating unit for processing the output signal so as to reduce a size of the image sensor, the image processor transforming the output signal to generate a combining signal, the signal interceptor intercepting a first part of the combining signal corresponding to a first clock period of the horizontal scan period to obtain a first signal, and intercepting a second part of the combining signal corresponding to a second clock period of the horizontal scan period to obtain a second signal, the calculating unit calculating the first signal and the second signal to obtain an image pixel data in accordance with a differential calculation, wherein, the number of clocks of the first clock period is the same as the number of clocks of the second clock period, and the image processor is disposed in the handle; and
a distal end, one end of the distal end connecting to the other end of the insert tube, the image sensor being disposed in the distal end.

10. The endoscope of claim 9, wherein the first clock period is the period of the 17th clock to the 340th clock of the horizontal scan period, and the second clock period is the period of the 357th clock to the 680th clock of the horizontal scan period.

11. The endoscope of claim 9, wherein the horizontal scan period comprises 680 clocks.

12. The endoscope of claim 9, wherein the first clock period and the second clock period comprise 324 clocks, respectively.

13. The endoscope of claim 9, wherein the combining signal comprises a third part and a fourth part, the signal interceptor intercepts the third part and the fourth part of the combining signal corresponding to a third clock period and a fourth clock period of the horizontal scan period to obtain a first sync signal corresponding to the first signal and a second sync signal corresponding to the second signal, respectively, the first sync signal and the second sync signal have a plurality of the clocks, respectively, and the first sync signal, the second sync signal, the first signal and the second signal are not overlapped with each other.

14. The endoscope of claim 13, wherein the combining signal comprises a fifth part and a sixth part, the signal interceptor intercepts the fifth part and the sixth part of the combining signal corresponding to a fifth clock period and a sixth clock period of the horizontal scan period to obtain a first blank signal and a second blank signal, respectively, the first blank signal and the second blank signal comprise a plurality of the clocks, respectively, and the first blank signal, the second blank signal, the first sync signal, the second sync signal, the first signal and the second signal are not overlapped with each other.

15. An endoscope, electronically connecting to a main device, comprising:
an insert tube;
a handle, one end of the handle connecting to one end of the insert tube;
an image processing system comprising an image sensor and an image processor, the image sensor receiving a plurality of light beams to output an output signal corresponding to a horizontal scan period, the image processor electronically connecting to the image sensor and comprising a signal interceptor and a calculating unit for processing the output signal so as to reduce a size of the image sensor, the image processor transforming the output signal to generate a combining signal, the signal interceptor intercepting a first part of the combining signal corresponding to a first clock period of the horizontal scan period to obtain a first signal and intercepting a second part of the combining signal corresponding to a second clock period of the horizontal scan period to obtain a second signal, the calculating unit calculating the first signal and the second signal to obtain an image pixel data in accordance with a differential calculation, wherein, the number of clocks of the first clock period is the same as the number of clocks of the second clock period, and the image processor is disposed in the main device; and
a distal end, one end of the distal end connecting to the other end of the insert tube, the image sensor being disposed in the distal end.

16. The endoscope of claim 15, wherein the first clock period is the period of the 17th clock to the 340th clock of the horizontal scan period, and the second clock period is the period of the 357th clock to the 680th clock of the horizontal scan period.

17. The endoscope of claim 15, wherein the horizontal scan period comprises 680 clocks.

18. The endoscope of claim 15, wherein the first clock period and the second clock period comprise 324 clocks, respectively.

19. The endoscope of claim 15, wherein the combining signal comprises a third part and a fourth part, the signal interceptor intercepts the third part and the fourth part of the combining signal corresponding to a third clock period and a fourth clock period of the horizontal scan period to obtain a first sync signal corresponding to the first signal and a second sync signal corresponding to the second signal, respectively, the first sync signal and the second sync signal have a plurality of the clocks, respectively, and the first sync signal, the second sync signal, the first signal and the second signal are not overlapped with each other.

20. The endoscope of claim 19, wherein the combining signal comprises a fifth part and a sixth part, the signal interceptor intercepts the fifth part and the sixth part of the combining signal corresponding to a fifth clock period and a sixth clock period of the horizontal scan period to obtain a first blank signal and a second blank signal, respectively, the first blank signal and the second blank signal comprise a plurality of the clocks, respectively, and the first blank signal, the second blank signal, the first sync signal, the second sync signal, the first signal and the second signal are not overlapped with each other.

\* \* \* \* \*